United States Patent [19]
Yoon

[11] Patent Number: 6,086,601
[45] Date of Patent: Jul. 11, 2000

[54] INSTRUMENT AND METHOD FOR SUTURING ANATOMICAL TISSUE AND TYING SUTURE MATERIAL

[76] Inventor: InBae Yoon, 2101 Highland Ridge Dr., Phoenix, Md. 21131

[21] Appl. No.: 09/300,467

[22] Filed: Apr. 28, 1999

Related U.S. Application Data

[60] Provisional application No. 60/083,521, Apr. 29, 1998.

[51] Int. Cl.$^7$ ................................. A61B 17/04
[52] U.S. Cl. ..................... 606/148; 606/139; 606/144; 606/147
[58] Field of Search ................... 606/139, 144, 606/145, 147, 148

[56] References Cited

U.S. PATENT DOCUMENTS

| | | | |
|---|---|---|---|
| 1,131,163 | 3/1915 | Saunders et al. | 606/145 |
| 1,155,378 | 10/1915 | Stedman | 606/145 |
| 1,916,722 | 7/1933 | Ende . | |
| 2,580,964 | 1/1952 | Skaller . | |
| 2,601,564 | 6/1952 | Smith | 606/147 |
| 4,109,658 | 8/1978 | Hughes . | |
| 4,257,420 | 3/1981 | Terayama . | |
| 4,557,265 | 12/1985 | Andersson . | |
| 4,636,638 | 1/1987 | Weintraub et al. | 606/147 |
| 5,037,443 | 8/1991 | Wilk et al. . | |
| 5,100,421 | 3/1992 | Christoudias | 606/147 |
| 5,152,769 | 10/1992 | Baber . | |
| 5,171,257 | 12/1992 | Ferzli . | |
| 5,209,741 | 5/1993 | Spaeth . | |
| 5,211,650 | 5/1993 | Noda . | |
| 5,222,508 | 6/1993 | Contarini . | |
| 5,224,948 | 7/1993 | Abe et al. . | |
| 5,234,443 | 8/1993 | Phan et al. . | |
| 5,261,917 | 11/1993 | Hasson et al. . | |
| 5,300,082 | 4/1994 | Sharpe et al. . | |
| 5,304,185 | 4/1994 | Taylor . | |
| 5,305,121 | 4/1994 | Moll . | |
| 5,308,353 | 5/1994 | Beurrier . | |
| 5,320,632 | 6/1994 | Heidmueller . | |
| 5,336,231 | 8/1994 | Adair . | |
| 5,364,409 | 11/1994 | Kuwabara et al. . | |
| 5,376,096 | 12/1994 | Foster . | |
| 5,389,103 | 2/1995 | Melzer et al. . | |
| 5,403,328 | 4/1995 | Shallman . | |
| 5,403,329 | 4/1995 | Hinchcliffe . | |
| 5,437,681 | 8/1995 | Meade et al. . | |
| 5,462,561 | 10/1995 | Voda . | |
| 5,462,562 | 10/1995 | Elkus . | |
| 5,468,251 | 11/1995 | Buelna . | |
| 5,470,338 | 11/1995 | Whitfield et al. . | |
| 5,474,568 | 12/1995 | Scott . | |
| 5,480,406 | 1/1996 | Nolan et al. | 606/139 |
| 5,496,310 | 3/1996 | Exconde et al. . | |
| 5,503,634 | 4/1996 | Christy . | |
| 5,540,705 | 7/1996 | Meade et al. | 606/147 |
| 5,601,575 | 2/1997 | Measamer et al. . | |
| 5,603,718 | 2/1997 | Xu . | |
| 5,607,435 | 3/1997 | Sachdeva et al. . | |
| 5,626,588 | 5/1997 | Sauer et al. . | |
| 5,632,751 | 5/1997 | Piraka . | |
| 5,632,752 | 5/1997 | Buelna . | |
| 5,643,292 | 7/1997 | Hart . | |
| 5,662,663 | 9/1997 | Shallman . | |
| 5,674,230 | 10/1997 | Tovey et al. . | |

(List continued on next page.)

FOREIGN PATENT DOCUMENTS

| | | |
|---|---|---|
| 482881A1 | 4/1992 | European Pat. Off. . |
| 337579 | 4/1904 | France . |
| 395073 | 8/1973 | U.S.S.R. . |
| 2260704 | 4/1993 | United Kingdom . |
| WO 97/37583 | 10/1997 | WIPO . |

*Primary Examiner*—Gary Jackson
*Attorney, Agent, or Firm*—Blank, Rome, Comisky & McCauley

[57] ABSTRACT

An instrument and method for suturing anatomical tissue with a suture needle and typing a knot in the suture material includes a barrel having two needle holders therein which can be manipulated from a proximal end of the barrel to cause the needle to pass through tissue and to pass the needle from one needle holder to the other to tie a knot in the suture material.

25 Claims, 10 Drawing Sheets

U.S. PATENT DOCUMENTS

| | | |
|---|---|---|
| 5,702,407 | 12/1997 | Kaji . |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. . |
| 5,810,805 | 9/1998 | Sutcu et al. . |

INSTRUMENT AND METHOD FOR SUTURING ANATOMICAL TISSUE AND TYING SUTURE MATERIAL

RELATED PATENT APPLICATION DATA

This application claims benefit of Provisional Application Ser. No. 60/083,521 filed Apr. 29, 1998.

This application is related to applicant's copending applications Ser. No. 08/847,254, Ser. No. 08/847,252, Ser. No. 08/899,710, Ser. No. 08/847,189, Ser. No. 08/847,182, Ser. No. 08/902,215, Ser. No. 08/905,215, Ser. No. 08/904,767, Ser. No. 902,311, Ser. No. 08/905,215, Ser. No. 08/847,253, Ser. No. 08/877,764, Ser. No. 08/847,189, and Ser. No. 08/904,764 the disclosures of which are incorporated herein by reference.

BACKGROUND OF THE INVENTION

1. Field of the Invention

The present invention pertains to suturing of bodily or anatomical tissue and, more particularly, to an apparatus and method for suturing anatomical tissue with suture material attached to a needle and tying the suture material with the same instrument.

2. Discussion of the Related Art

Suturing of bodily tissue, that is, the practice of using lengths of suture material to ligate or approximate tissue, is a time consuming part of most surgical procedures including open surgery, microsurgery and minimally invasive surgery. "Open surgery" refers to surgery wherein the surgeon gains access to the surgical site by a relatively large incision and "minimally invasive surgery" refers to any type of surgery, such as endoscopic surgery or "mini-lap" surgery, wherein the surgeon gains access to the surgical site via one or more portals or small incisions through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue one or more times, the surgeon ties a knot in the suture material. The knot tying procedure allows the surgeon to adjust the tension on the suture material to accommodate the particular tissue being sutured and to control approximation, occlusion, attachment or other conditions of the tissue.

The process of tissue penetration and tying a knot in the suture material can be time consuming and tedious work, particularly when performed in connection with microsurgery and minimally invasive surgery and can unduly prolong the duration of surgery and therefore the period in which the patient is under anesthesia. Nevertheless, minimally invasive surgery is preferred over open surgery due to the greatly reduced trauma and wound healing time for the patient and due to cost savings associated with shorter hospital stays and performing surgery in non-hospital or outpatient surgery sites. Accordingly, there has been much effort to develop techniques to replace the suturing normally performed by use of a suture needle and a length of suture material. Alternative techniques include electrical coagulation, mechanical devices such as clips, clamps and staples, and lasers.

However, no alternative technique has yet been well accepted by surgeons to produce the results obtained by suturing and knot tying. Thus, there is a great need for suturing and knot tying techniques useful in minimally invasive surgery, open surgery, and microsurgery to permit surgeons to suture anatomical tissue with suture material attached to a needle and tie a knot in the suture material in a time efficient consistent, and precise manner.

The performance of a minimally invasive procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments having scissors, forceps, needle holders, and the like, into the anatomical cavity. The portal sleeve can be omitted and instruments can be inserted through a very small incision.

Suturing is typically performed with a needle holding instrument, or needle holder, having a needle holding member, such as a pair of jaw members adapted to hold the body of a suture needle. The jaw members of the needle holding instrument are inserted into the cavity and are positioned at the operative site by manipulation of a handle at the proximal end of the instrument outside the body. With a suture needle held between the jaw members of the needle holding instrument, the handle is manipulated to cause a tip of the needle to be pushed through the tissue being sutured. Once the tip of the suture needle has been pushed through the tissue, the jaw members of the needle holding instrument must be opened to release the suture needle so that the tip of the needle can be grasped and pulled through the tissue therewith, or, after opening the jaw members, a second needle holding instrument must be introduced at the operative site through another portal to grasp the tip of the suture needle after it has emerged from the tissue being sutured.

The former technique requires difficult manipulation and further adjustment of the suture needle within the jaw members of the needle holder before another stitch can be made. While use of a second needle holding instrument for pulling the needle through the anatomical tissue allows the first needle holding instrument to grasp the body of the suture needle in the manner required to make additional stitches, a second puncture site is required to permit insertion of the second instrument. It is generally desirable to minimize the number of puncture sites created for performing a particular endoscopic procedure. Because of the difficulty in manipulating a needle and suture material noted above it is difficult to tie a knot in the suture material after suturing, particularly in minimally invasive procedures and open procedures conducted in small spaces or cavities. Several methods of tying suture material, and alternatives to tying suture material, have been proposed.

One approach has been to use a mechanical clamp, sometimes known as a "knotting element", to fix suture material in place after suturing, in leu of tying a knot in the suture material. U.S. Pat. Nos. 5,409,499, 5,474,572, and 5,669,935 all disclose examples of knotting elements. However, knotting elements can be cumbersome to apply and often require additional instruments thus complicating the surgical procedure. Another approach has been to tie a knot externally of the anatomical cavity and to push the knot along suture material into the anatomical cavity with a "knot pusher". Examples of externally tied knotting procedures and instruments therefor are disclosed in U.S. Pat. Nos. 5,391,175, and 5,397,326. However, externally tying the knot requires some means for pushing or guiding the knot into place and renders it difficult to tighten the knot properly to apply the desired tension to the suture material after suturing.

Another approach has been to introduce a single dedicated knot tying instrument, or multiple dedicated knot tying instruments, into the anatomical cavity to tie a knot in suture material. Of course, the use of dedicated knot tying instruments increases the number of instruments and the manual dexterity required for a procedure. Examples of known instruments for tying knots in suture material are disclosed in U.S. Pat. Nos. 5,147,373, 5,336,230, and 5,234,443. However, the instruments and methods of tying a knot disclosed in U.S. Pat. Nos. 5,234,443, 5,147,373, and 5,336,230 require complex manipulation of the suture material with a grasping device. These methods are cumbersome because the suture material must be grasped.

SUMMARY OF THE INVENTION

Accordingly, it is a primary object of the present invention to improve instruments and methods of tying suturing material after suturing anatomical tissue.

It is another object of the invention to permit a knot to be tied in suture material through the same manipulation used for suturing tissue with the suture material.

It is a further object of the present invention to permit a suturing and knot tying instrument as well as other instruments and devices to be introduced through a single portal or other opening in a minimally invasive procedure without having to withdraw the suturing instrument from the portal or other opening.

It is still a further object of the invention to tie a knot in suture material by passing a needle attached to the suture material from one needle holder to another without releasing the needle.

Finally, it is an object of the invention to control a minimally invasive or open surgical knot tying procedure with standard proximal end controls.

The present invention allows suturing of anatomical tissue and tying a knot in suture material to be accomplished in a time efficient, consistent and precise manner. A first aspect of the present invention is generally characterized in an instrument for suturing anatomical tissue with a suture needle and tying a knot in suture material including a barrel, a needle driver and a needle catcher. The needle driver and the needle catcher each include needle holding members, movable relative to one another to permit a needle to be passed therebetween and selectively grasped in either one of the needle driver or needle catcher. When needle holding members of the needle driver are operated to grasp the suture needle, the needle driver can be operated to drive the suture needle through anatomical tissue positioned between the needle driver and the needle catcher, and when the needle holding members of the needle catcher are operated to grasp the suture needle, the needle holding members of the needle driver can be operated to release the suture needle, thereby allowing the needle catcher to be operated to pull the suture material through the anatomical tissue. When a suturing procedure is completed, the needle driver and needle catcher can be operated so that the needle can be passed between the needle driver and the needle catcher to tie a knot in the suture material. Specifically, a distal end of the instrument is moved away from the sutured tissue and the needle is passed between the needle driver and the needle catcher to tie a knot in the suture material without releasing the needle.

Another aspect of the present invention is generally characterized in a method of suturing anatomical tissue using a length of suture material attached to a suture needle by passing a needle from a needle driver to a needle catcher and tying a knot in the suture material by passing the needle from the needle driver to the needle catcher. The method includes the steps of grasping the suture needle with needle holding members of a needle driver, positioning the anatomical tissue between a tip of the suture needle and a needle catcher, moving the needle driver to cause the tip of the needle to penetrate the anatomical tissue, receiving the tip of the suture needle in needle holding members of the needle catcher, grasping the suture needle with the needle catcher, releasing the suture needle from the needle driver, moving the needle catcher to pull the needle and the suture material through the anatomical tissue, moving the needle driver and the needle catcher away from the sutured material, and tying a knot in the suture material by passing the needle from the needle catcher to the needle driver and back to the needle catcher.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

The invention is described through preferred embodiments and the attached drawing in which.

DETAILED DESCRIPTION OF THE PREFERRED EMBODIMENTS

The suturing and tying instrument of the present invention can be utilized to suture any type of anatomical tissue and tie a knot in suture material of any type in any procedure. Accordingly, while the instrument is described hereinafter for use in minimally invasive procedures, such as endoscopic procedures, the instrument can be used in open surgery and with catheters and other small and large diameter tubular or hollow cylindrical members providing access to small cavities, such as veins and arteries, as well as large cavities, such as the abdomen. The term "suturing" as defined herein refers to passing a needle through tissue one or more times while suture material is attached to the needle to pull the suture material through the tissue. The phrase "knot tying" as defined herein refers to forming a knot or other locking configuration in the suture material to fix the suture material in place after a suturing procedure. The term "needle" as defined herein refers to any member having suture attached thereto and which can be passed through tissue.

Figure 1:
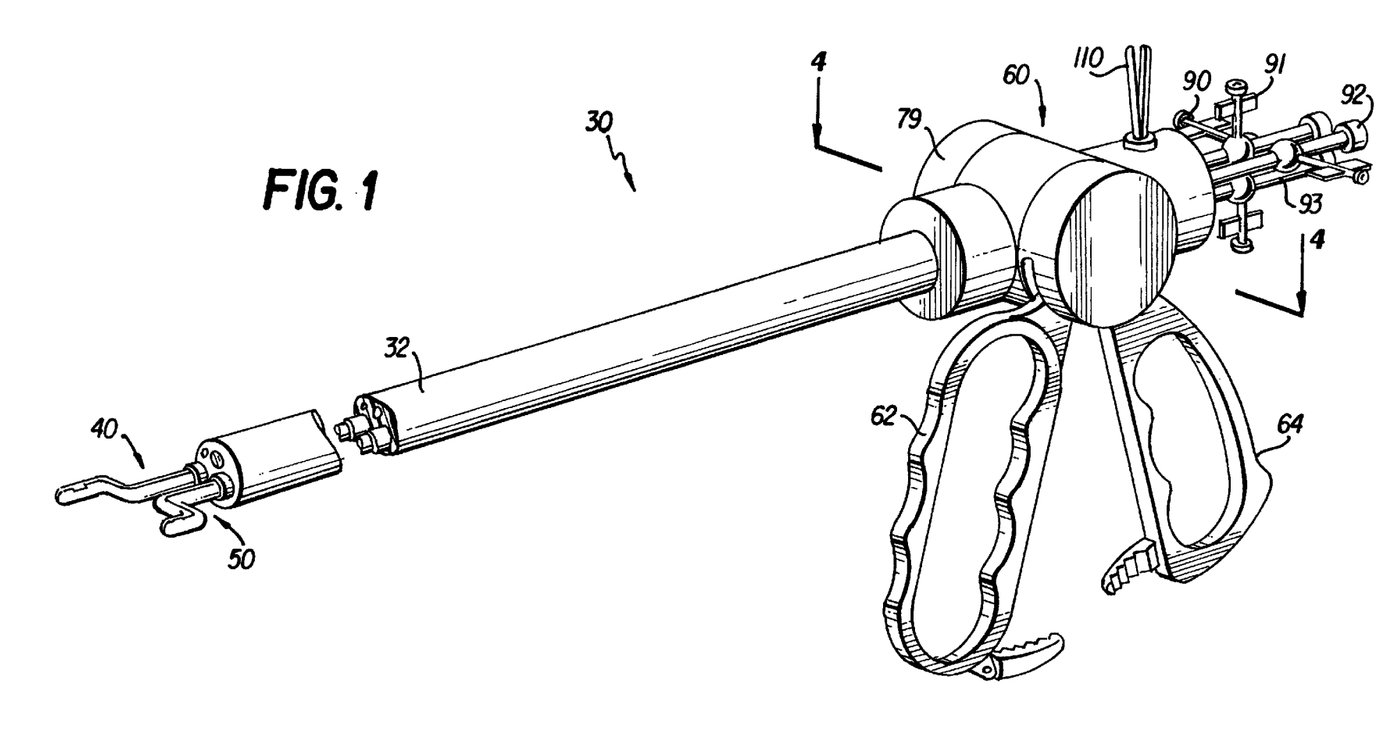
FIG. 1 is a perspective view of an instrument according to the invention.

A suturing and knot tying instrument according to the present invention is illustrated at 30 in FIG. 1 and includes cylindrical barrel (or outer shaft) 32, needle driver 40, and needle catcher 50. Needle driver 40 and needle catcher 50 are substantially contained within cylindrical barrel 32 as is described in detail below. The terms "needle driver" and "needle catcher" are used herein to describe, in terms of their function, elements that may be structurally similar in the preferred embodiment. However, the function of these two elements herein is interchangeable. Also, these elements are sometimes referred to generically as "needle holders" herein. Needle driver 40 and needle catcher 50 optionally can be moved proximally and distally in barrel 32.

Figure 2:
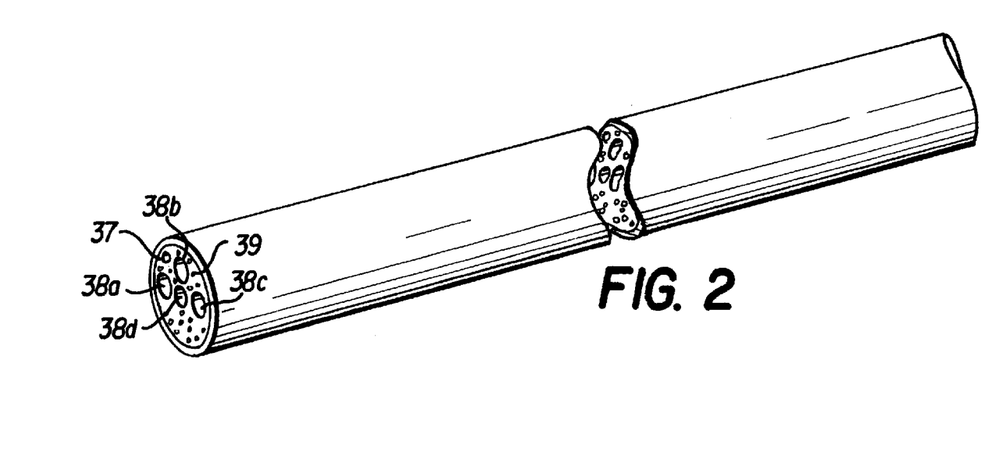
FIG. 2 is a perspective view of a portion of the barrel of the instrument of FIG. 1.

As shown in FIG. 2, barrel 32 has operating channels 38a–d and suture material passage 37 extending longitudinally therethrough. Barrel 32 can have additional channels for receiving one or more additional instruments to be introduced in the abdominal cavity or barrel 32 can have fewer channels as needed. Optical fibers 39 extend through barrel 32 to transmit light from a proximal light source to the body cavity of a patient. Channels 38a–d can be formed by thin wall, tubular sleeves extending longitudinally through barrel 32 or by any other means.

Figure 3:
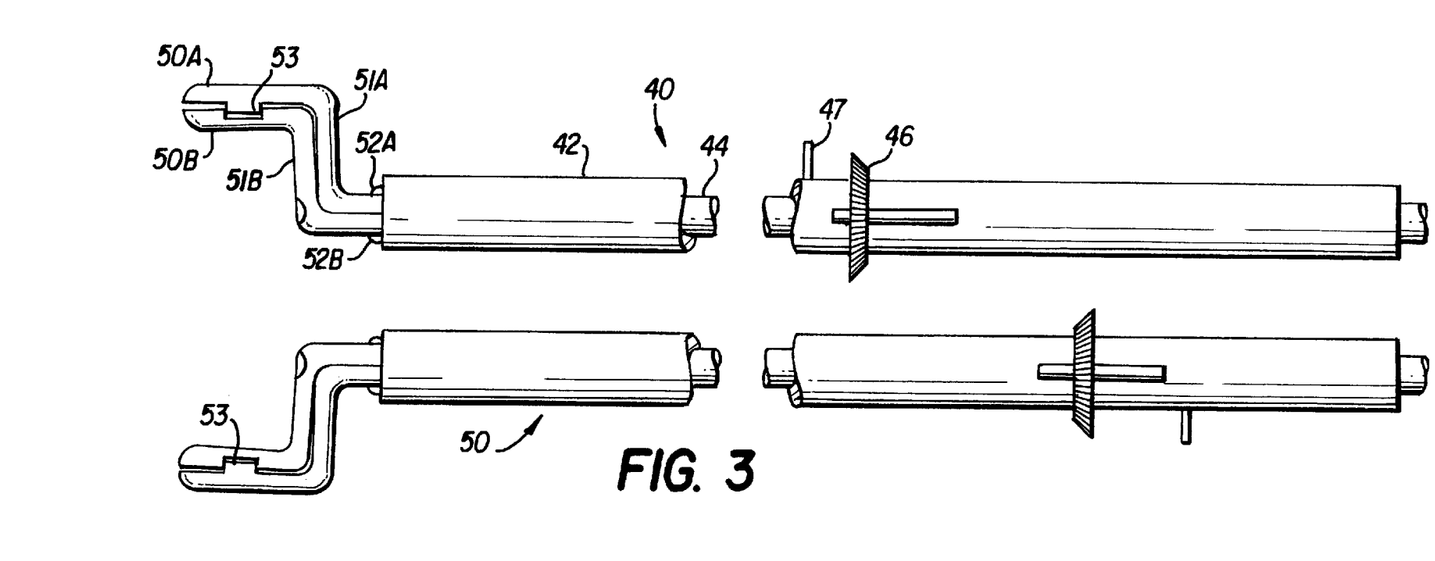
FIG. 3 is a side view of a needle driver and a needle catcher of the instrument of FIG. 1 removed from the barrel for illustrative purposes.

FIG. 3 illustrates needle driver 40 and needle catcher 50 removed from barrel 32 for illustrative purposes. Needle driver 40 includes elongated, tubular outer member 42 and elongated tubular inner member 44 disposed within outer member 42. Outer member 42 and inner member 44 define a shaft that is rotatable in barrel 32. Outer member 42 has a proximal end on which beveled gear 46 is disposed. Projection 47 extends from outer member 42. The function of beveled gear 46 and projection 47 is described in detail below.

Figure 7:
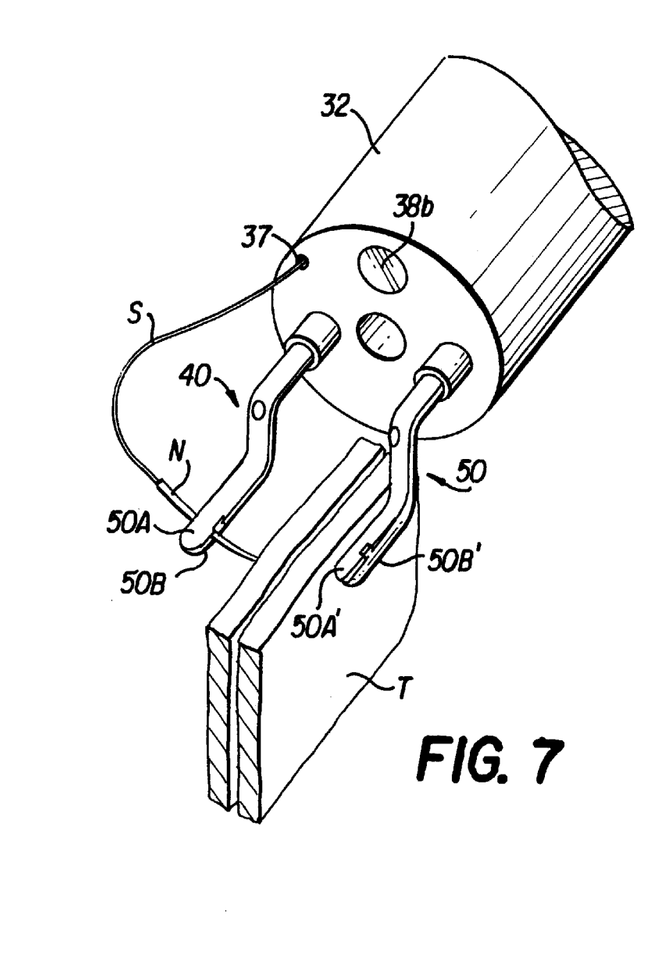
FIGS. 7–11 are perspective views illustrating a suturing operation utilizing the instrument, FIG. 1.

Arms 51A and 51B serve as connecting members between jaw members 50A and 50B and inner member 44 and can be made entirely or partly of resilient, flexible or spring materials, or materials having shape memory. Jaw members 50A and 50B serve as a needle holding member and are biased to be normally disposed to an open position wherein the jaw members have a gap defined therebetween. This permits the shank of a suture needle to be placed between jaw members 50A and 50B and to be grasped thereby. Of course, the inner surfaces of jaw members 50A and 50B can be shaped to correspond to the needle shank, or any other appropriate way, to firmly grasp the needle when the jaw members 50A and 50B are in a closed position as shown in FIG. 7. Cam surfaces 52A and 52B are formed on arms 51A and 51B respectively. Movement of outer member 42 in a distal direction with respect to inner member 44 causes outer member 42 to push at least partially over cam surfaces 42A and 42B to close jaw members 50A and 50B. Needle driver 40 can be designed in various known ways permitting jaw members 50A and 50B to be movable between the closed position and the open position. The opening and closing movement of jaw members 50A and 50B is described in more detail below.

Needle catcher 50 includes elongated, tubular outer member 42' and elongated tubular inner member 44' disposed within outer member 42'. Outer member 42' and inner member 44' define a shaft that is rotatable in barrel 32. Outer member 42' has a proximal end on which beveled gear 46' is disposed. Projection 47' extends from outer member 42'. The function of beveled gear 46' and 47' is described in detail below. 51A' and 51B' serve as connecting members or arms between jaw members 50A' and 50B' and inner member 44' and can be made entirely or partly of resilient, flexible or spring materials, or materials having shape memory. Jaw members 50A' and 50B' serve as a needle holding member and are biased to be normally disposed to an open position wherein the jaw members have a gap defined therebetween. This permits the shank of a suture needle to be placed between jaw members 50A' and 50B' and to be grasped thereby. A longitudinal axis of the jaw is parallel to and offset from the corresponding shaft. Of course, the inner surfaces of jaw members 50A' and 50B' can be shaped to correspond to the needle shank, or any other appropriate way, to firmly grasp the needle when jaw members 50A' and 50B' are in a closed position as shown in FIG. 7. Cam surfaces 52A' and 52B' are formed on arms 51A' and 51B' respectively. Movement of outer member 42' in a distal direction with respect to inner member 44' causes outer member 42' to push at least partly over cam surfaces 42A' and 42B' to close jaw members 50A' and 50B'. Needle catcher 50 can be designed in various known ways permitting jaw members 50A' and 50B' to be movable between the closed position and the open position. The opening and closing movement of jaw members 50A' and 50B' also is described in more detail below.

Needle driver 40 and needle catcher 50 can be of any configuration which permits selective grasping of the needle and relative motion between the needle driver and needle catcher, and can include needle holding members such as pivoting jaw members, slots and keepers, and moveable flanges. For example, the needle driver and needle catcher can have any of the configurations disclosed in the related applications noted above, the disclosures of which are incorporated herein by reference.

Figures 4, 5, 6:
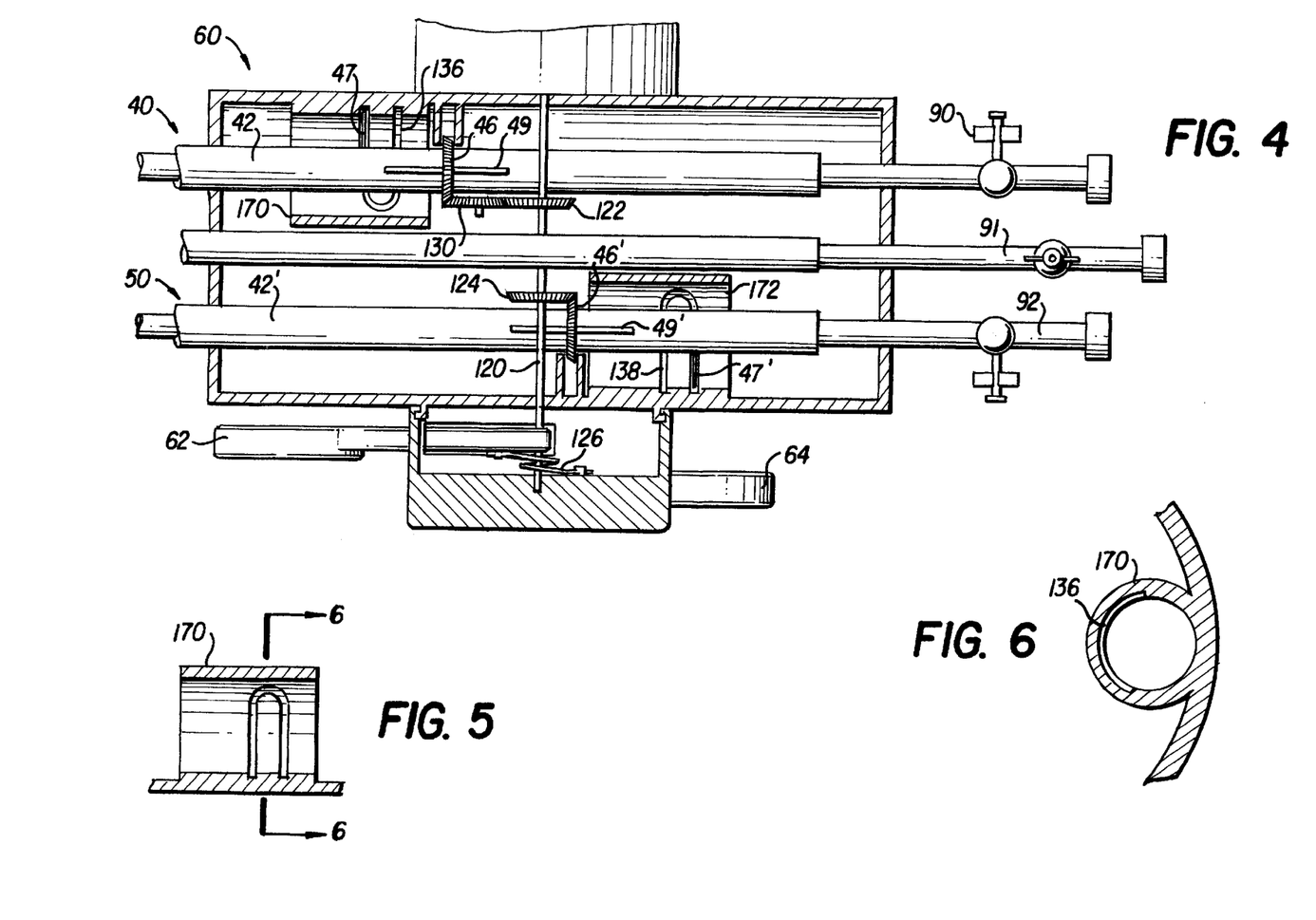
FIG. 4 is a partial sectional view of a portion of the instrument of FIG. 1 taken along 4—4 of FIG. 1 illustrating the internal mechanism for operating the needle driver and the needle catcher.
FIG. 5 is a sectional view of a portion of the instrument taken along line 4—4 of FIG. 1.
FIG. 6 is a sectional view taken along line 6—6 of FIG. 5.

As illustrated in FIGS. 1 and 4, proximal controls 60 of the preferred embodiment include a set of scissor type handles 62 and 64 extending out of housing 79 disposed on a proximal end of barrel 32. Handle 62 can be pivoted towards handle 64 to cause movement of the shafts of needle driver 40 and needle catcher 50 and jaw members 50A and 50B and jaw members 50A' and 50B', in a coordinated manner as is discussed in detail below. Handle 62 is coupled to both needle driver 40 and needle catcher 50 in a manner which causes the desired rotation of the shafts of needle driver 40 and needle catcher 50 and the opening and closing operation of the respective jaws necessary for passing the needle between needle driver 40 and needle catcher 50 merely by squeezing and releasing handles 62 and 64 once or multiple times. The mechanism coupling handles 62 and 64 to needle driver 40 and needle catcher 50 can be designed to accomplish any stitching or tying function disclosed below or any other appropriate motion. Such an automatic mechanism facilitates suturing by minimizing fatigue on the surgeon and reducing the possibility of operational errors.

FIGS. 4–6 illustrate an internal mechanism of proximal controls 60 in detail. Handle 64 is fixedly connected to housing 79. Handle 62 is movable and extends through a slot in housing 79 to be mounted on shaft 120 to cause shaft 120 to rotate when handle 62 is pivoted towards handle 64. Beveled gears 122 and 124 are also mounted on shaft 120 to rotate with shaft 120. Biasing member 126, shown as a coiled spring, biases handle 62 away from handle 64 to the illustrated position.

Beveled gears 122 and 124 are coupled respectively to beveled gears 46 and 46' that are mounted on outer member 42 and outer member 42' respectively. Note that beveled gears 46 and 46' are axially slidable with respect to outer members 42 and 42' respectively, but are fixed rotationally on the outer members by keys 49 and 49'. Beveled gear 124 is coupled directly to beveled gear 46' and beveled gear 122 is coupled to beveled gear 46 through beveled gear 130. Accordingly, rotation of shaft 120 causes outer member 42 to rotate in a first direction and causes outer member 42' to rotate in a second direction opposite to the first direction. The corresponding inner members are configured to rotate with the outer members.

Projection 47 extends from outer member 42. A free end of projection 47 slides in cam groove 136 formed in cylindrical member 170 fixed to housing 79. Similarly, projection 47' extends from outer member 42' and slides in cam groove 138 formed in cylindrical member 172. The cam grooves are shaped to cause the respective outer members to move axially, in distal and proximal directions, after the outer members rotate through a predetermined angle.

In operation, a needle is grasped in jaws of needle driver 40 with proximal controls 60 in the position illustrated in FIG. 4. When the surgeon squeezes handle 62 towards handle 64, shaft 120 rotates to cause needle driver 40 to rotate in a counter clockwise direction, as viewed from the distal end, and simultaneously to cause needle catcher 50 to rotate in a clockwise direction, as viewed from the distal end. This results in the needle being pushed through tissue and into the jaws of needle holder 50 at which time cam grooves 136 and 138 cause outer members 42 and 42' to move relative to inner members 44 and 44' respectively in a manner to open jaws of needle driver 40 and close jaws of needle catcher 50. Specifically, as outer member 42 rotates counter-clockwise projection 47 enters the curved portion of cam groove 136 to cause outer member 42 to move proximally with respect to inner member 44. Therefore, outer member 42 moves off of cam surfaces 42A and 42B to allow jaw members 50A and 50B to open. Similarly, the interaction between projection 47' and cam groove 138 causes outer member 42' to move distally and close jaw members 50A' and 50B' around the needle.

Releasing handles 62 and 64 permits needle holder 40 and needle catcher 50 to rotate in opposite directions due to the force of biasing member 126 as projections 47 and 47' continue in the same direction through cam grooves 136 and 138. Now handles 62 and 64 can be compressed again to transfer the needle back to needle driver 40 for another stitch or for tying a knot in the manner described below with the appropriate jaws operating in a coordinated manner. Note that handles 62 and 64 are configured to be grasped while the surgeon's fingers pass through openings in the handles or while the surgeon's fingers are wrapped around outer portions of the handles to increase comfort and adaptability.

It will be appreciated that the jaw members of needle driver 40 and needle catcher 50 can be of different configurations, such as those described in the related applications incorporated herein, dependent upon procedural use and other considerations. Also, cutting elements 53 can be provided on the jaw members as needed to cut suture material or tissue, as illustrated in FIG. 3.

It can be seen that pressing handle 62 towards handle 64 moves the jaws of the needle driver 40 toward the needle catcher and releasing handle 64 moves the jaws of the needle driver away from the jaws of the needle catcher. Once the needle has been pulled through the tissue, the mechanism can reverse the process so that, for example, if the handle is squeezed again, the mechanism will cause the jaws of the needle catcher to rotate toward the needle driver while also causing the jaw members of the needle catcher to open and the jaw members of the needle driver to close, thereby transferring the suture needle back to the needle driver for continued suturing. This same automatic motion of the needle holders can be used for tying a knot merely by manipulating the distal end of the instrument in the manner disclosed below.

Suture material channel 37 extends to a proximal aperture (not illustrated) through which suture material S is supplied. Excess suture material may be stored on a spool or in a container. The surgeon can grasp proximal portions of suture material S to retract suture material S and fix proximal portions of suture material S in the manner described below. Alternatively, the retracting and fixing functions can be accomplished by a mechanism for turning a spool, a clamping device, a braking device, or any other mechanism for achieving the retracting and fixing function disclosed below. A distal end of suture material S is attached to needle N and needle N is loaded in jaw members 50A and 50B of needle driver 40. Suture material S can be inserted through suture material passage 37, prior to a suturing procedure, with a rigid guide tool or the like that is removed after a distal end of suture material S extends out of a distal end suture material passage 37.

In use, suturing instrument 30 is inserted into a body cavity using known techniques. Note that the entire device can be inserted through a single puncture site. Also, jaw members 50A and 50B and 50A' and 50B' as well as needle N, which can be initially grasped by needle driver 40, can be disposed within the diametrical dimension of barrel 32 by positioning needle driver 40 and needle catcher 50 appropriately. By grasping proximal controls 60, the distal end of suturing instrument 30 is guided to the operative site through a portal sleeve positioned in the wall of an anatomical cavity. The portal sleeve can be positioned in the anatomical cavity wall using any suitable penetrating technique, including those creating puncture sites by means of a removable obturator, such as a trocar, and can include a valve housing, if desired, to prevent loss of pneumoperitoneum during insertion and withdrawal of the instrument. Further, a retractable sheath can be provided to facilitate insertion through a portal sleeve valve by protecting needle driver 40 and needle catcher 50. Visualization of the endoscopic procedure can be accomplished using a conventional endoscope incorporated into channel 38b, for example (known as a single puncture procedure) or separately positioned within the anatomical cavity through a second portal sleeve located at another puncture site (known as a double puncture procedure).

Prior to insertion through a portal sleeve or the like, needle N is held tightly between jaw members 50A and 50B of needle driver 40. Alternatively, needle N can be introduced into the body cavity by a separate instrument through a separate puncture sight or through an operating channel of instrument 30. In this embodiment, needle N is curved. However, needle N can be straight or of any other appropriate shape.

Figure 8:
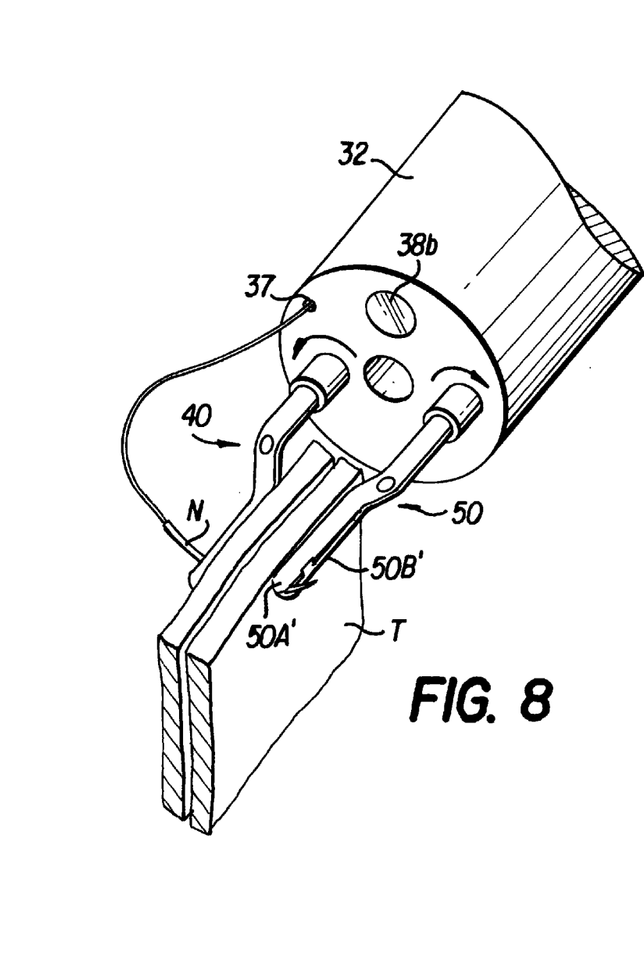

FIGS. 7–19, illustrate a suturing and knot tying procedure after insertion of the distal end of instrument 30 into a body cavity. As illustrated in FIG. 7, needle N, having suture material S attached thereto, is grasped between jaw members 50A and 50B of needle driver 40. The distal end of instrument 30 is then manipulated to place tissue T (to be sutured) between a tip of needle N and jaw members 50A' and 50B' of needle catcher 50, as shown in FIG. 7. Handle 62 is then pressed toward handle 64 and thus the shaft of needle holder 40 is rotated in a counter-clockwise direction as viewed in FIGS. 7–19 to cause a tip of needle N to penetrate and pass through a portion of tissue T while a shaft of needle catcher 50 is simultaneously rotated in a clockwise direction. Therefore, jaw members 50A and 50B push needle N through tissue T and into jaw members 50A' and 50B', as illustrated in FIG. 8. Jaw members 50A and 50B open due to movement of outer member 42, as described above, and jaw members 50A' and 50B' close due to distal movement of outer member 42', as described above.

Figure 9:
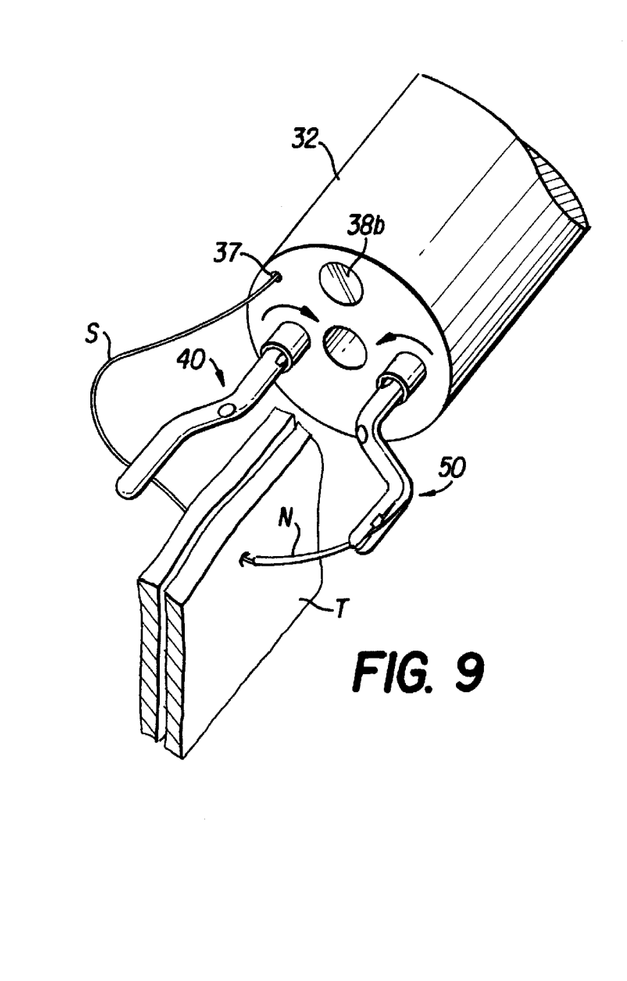
Figure 10:
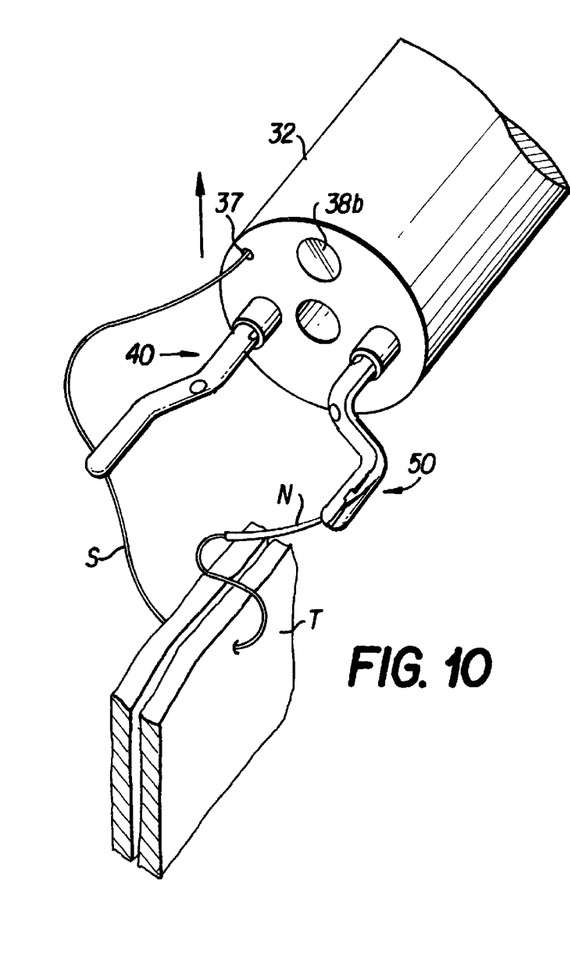
Figure 11:
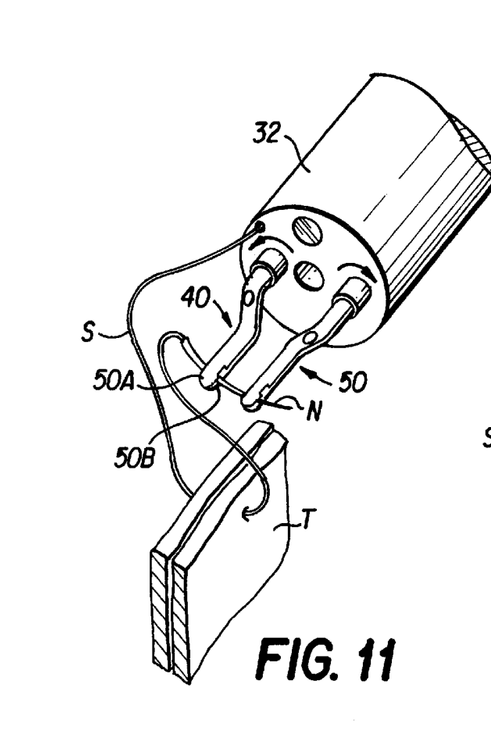
Figure 12:
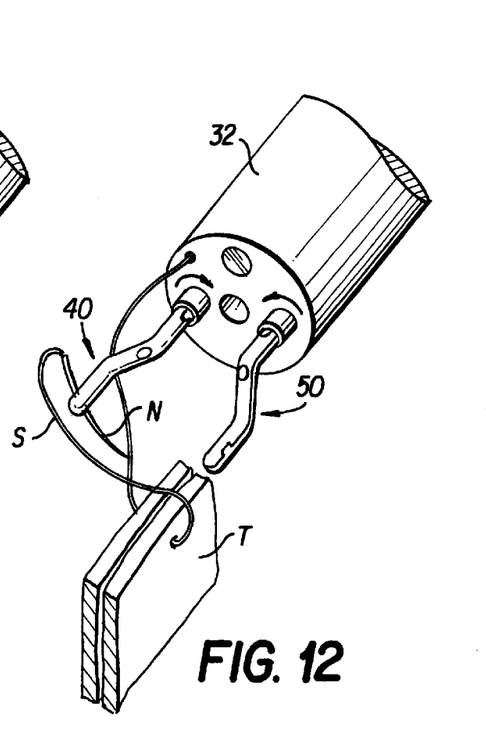
FIGS. 12–20 are perspective views illustrating a knot tying procedure utilizing the instrument, FIG. 1.

With needle N positioned in needle catcher 50, handle 62 is released with needle N grasped between jaw members 50A' and 50B' and the shaft of needle catcher 50 is rotated in a counter-clockwise direction to pull needle N and thus suture material S attached to needle N, through tissue T, as illustrated in FIG. 9. As shown in FIG. 10, after needle N has been pulled through tissue T, the distal end of instrument 20 can then be moved away from tissue T (upwards in the drawing) and handle 62 can be compressed again so needle catcher 50 is rotated clockwise and needle driver 40 is rotated in a counter clockwise direction to place needle N between jaws 50A and 50B and needle N is grasped again with jaw members 50A and 50B, as shown in FIG. 11. In this state a single stitch has been made and upon releasing handle 62 instrument 30 is returned to the position illustrated in FIG. 12 and ready to make subsequent stitches, if needed. Of course, the suturing procedure can be conducted by manipulating needle driver 40 and needle catcher 50 in any appropriate manner, such as the suturing procedures disclosed in the related applications incorporated herein. For example, the needle holders can be manipulated independently in seriatim or automatically in seriatim.

Figure 13:
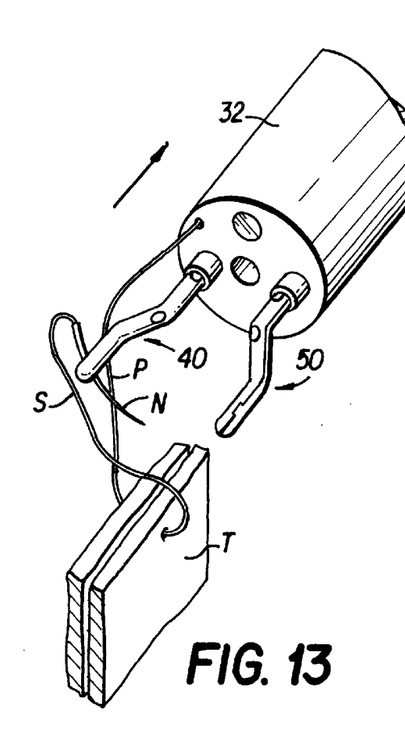
Figure 14:
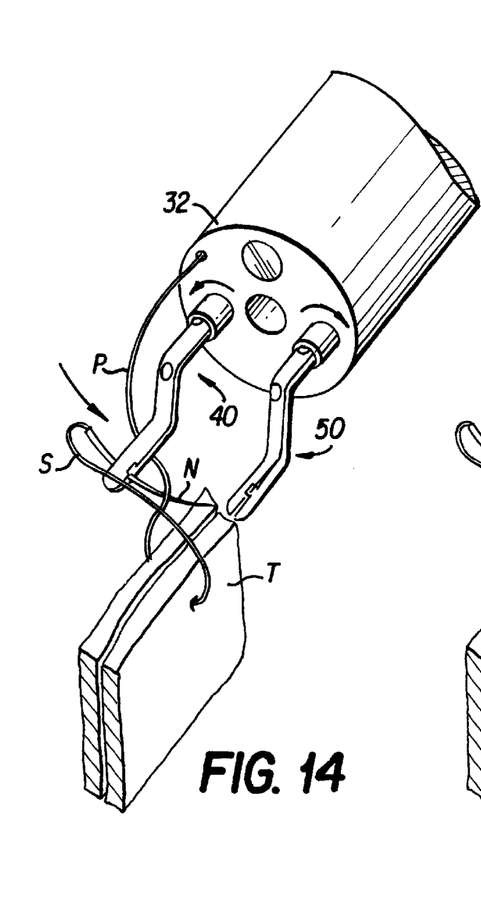
Figure 15:
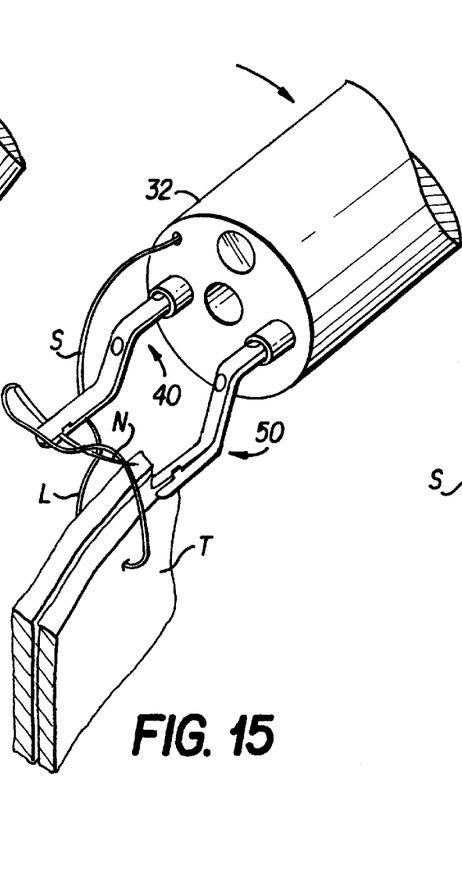
Figure 16:
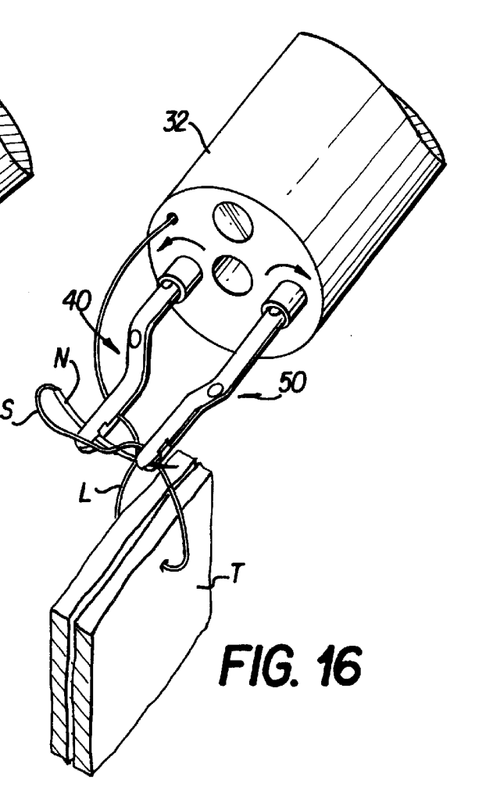
Figure 17:
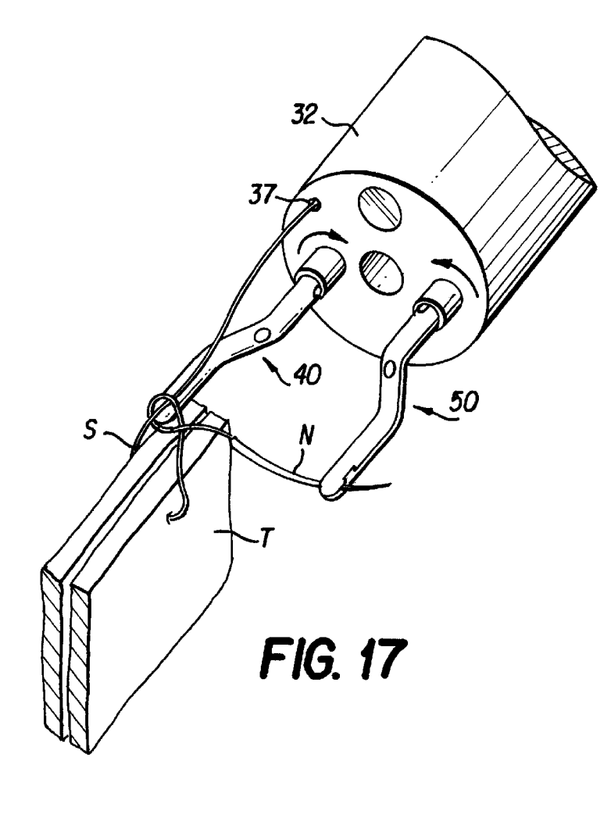
Figure 18:
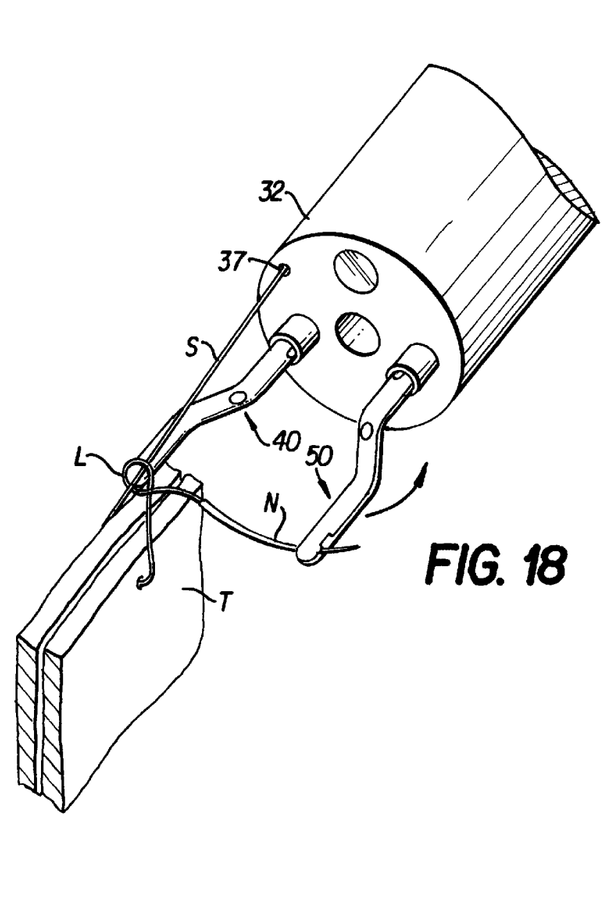
Figure 19:
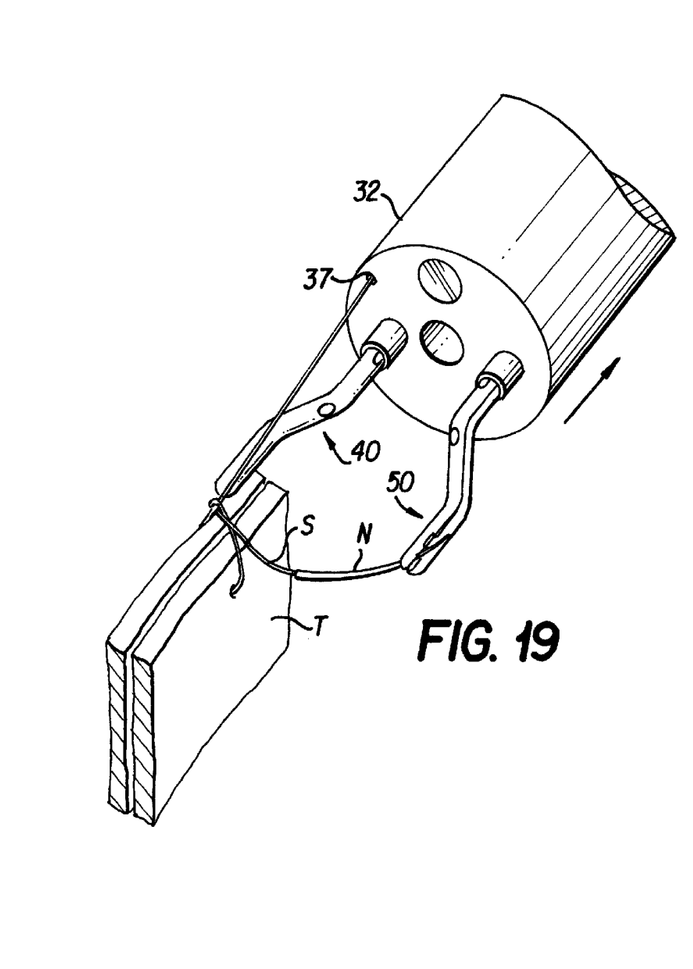
Figure 20:
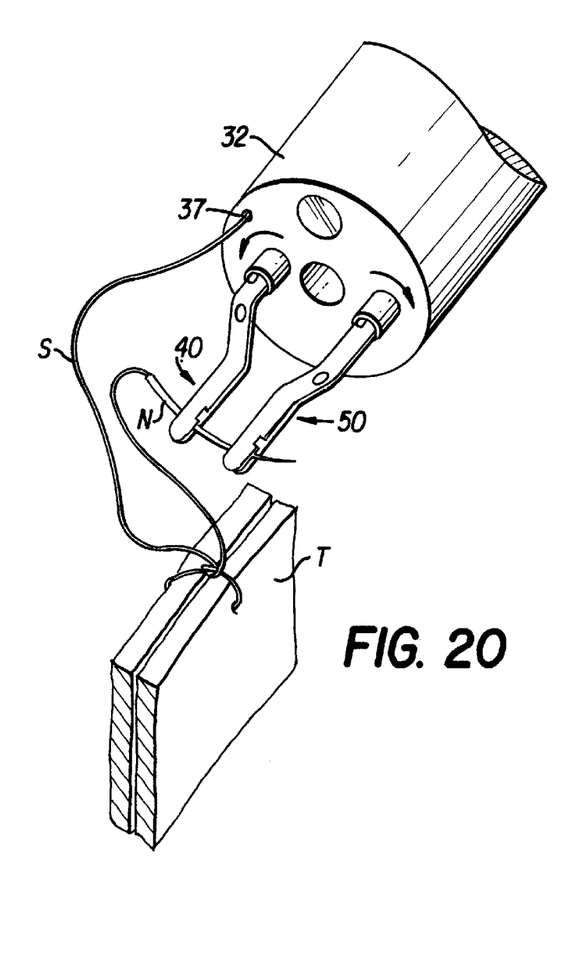

Once the desired number of stitches have been made in the tissue in the manner described above, the surgeon can begin a knot tying procedure. As illustrated in FIG. 13, instrument 30 is moved proximally in a direction out of the cavity over a distance that is adequate to position the tip of needle N behind a trailing portion P of suture material S. In this state, handle 62 can be compressed partially so needle driver 40 is again rotated in a counter-clockwise direction and needle catcher 50 is rotated in a clockwise direction to pass the tip of needle N behind trailing portion P of suture S, as illustrated in FIG. 14. As illustrated in FIG. 15, while handle 62 is partially compressed, barrel 32 of instrument 30 is pivoted in the direction of the arrow to direct the tip of needle N to extend through loop L formed by suture material S, and handle 62 is compressed further so needle driver 40 is rotated further in a counter-clockwise direction to push the tip of needle N through loop L and into jaw members of needle catcher 50 as needle catcher 50 simultaneously rotates in a clockwise direction. Accordingly, the tip of needle N is grasped by jaw members 50A' and 50B' of needle catcher 50, and released by jaw members 50A and 50B of needle driver 40 as illustrated in FIG. 16. Release of handle 62 will cause needle catcher 50 to be rotated counter-clockwise to the position illustrated in FIG. 17. From the position of FIG. 17, suture material S can be drawn into suture material channel 37, by the surgeon grasping proximal portions of suture material S, as shown in FIG. 18, and instrument 30 is manipulated to move needle catcher 50, as shown in FIG. 19, to tighten loop L around tissue T. Needle N can then be passed back into jaw members 50A and 50B of needle driver 40, as shown in FIG. 20, by compressing handle 62, for tying another "hitch" in the manner described above.

The knot can comprise any number of hitches, preferably two or more. Cutting elements 53 can be used to cut suture material S, by manipulating the appropriate jaw members, to permit withdrawal of instrument 30 and needle N.

Figure 21:
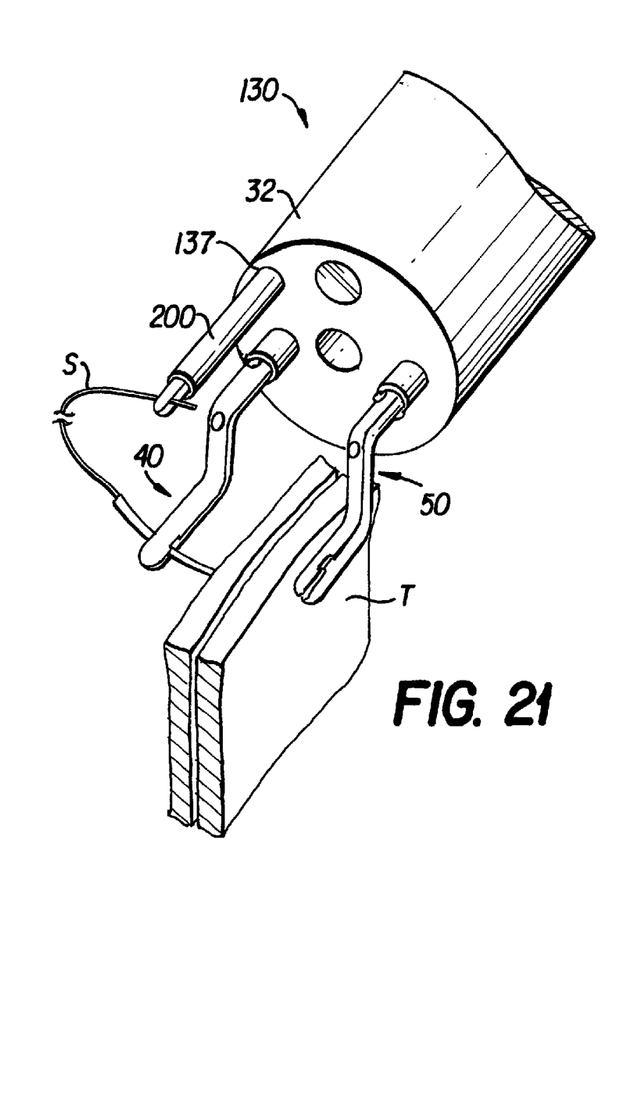
FIG. 21 illustrates another instrument according to the invention.
Figure 22:
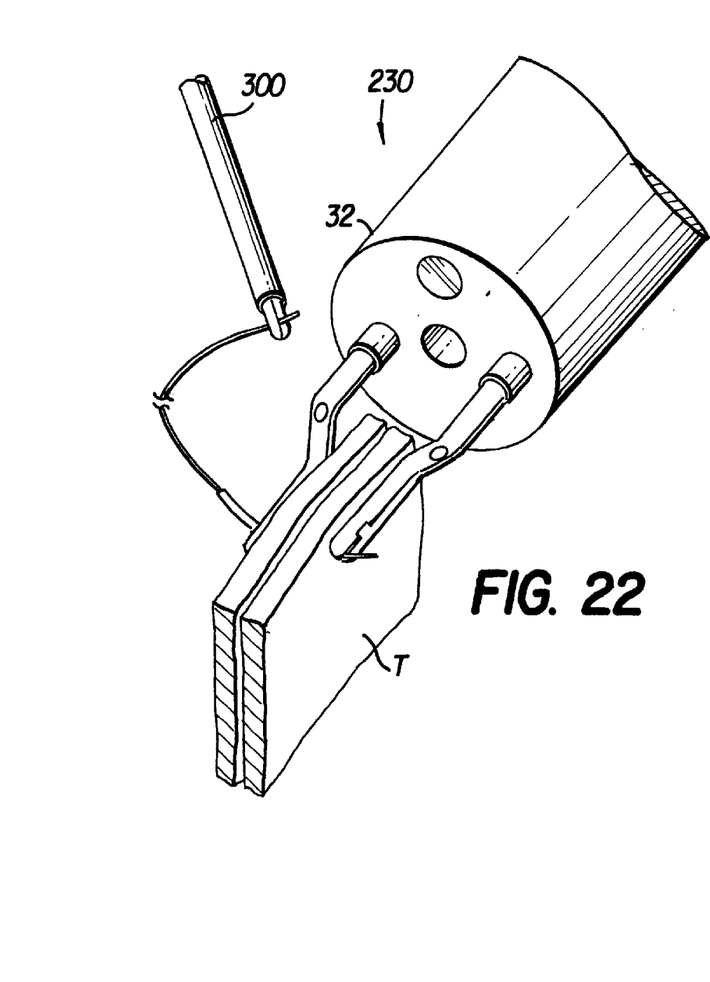
FIG. 22 illustrates another instrument according to the invention.

FIG. 21 illustrates a suturing and knot tying procedure using another instrument 130 according to the invention. Instrument 130 has a suture material grasping instrument 200 inserted through operating channel 137. Jaw members of grasping instrument 200 hold suture material S at the proximal end of instrument 130 to manipulate and tension suture material during a suturing procedure and a knot tying procedure. Other portions of instrument 130 and the operation thereof are similar to instrument 30. FIG. 22 illustrates instrument 230 which is used with suture grasping instrument 300 introduced through a separate puncture or otherwise separately introduced to an area proximate tissue T.

Note that needle N can be straight or curved. Also, suture S can be connected to any portion of needle N and needle N can be stored in an operating channel prior to suturing. Further, the suturing and tying motion can be accomplished by rotating barrel 32 in its entirety with the needle holders temporarily locked in position relative to barrel 32. At any point during the operative procedure, channel 38d can be used for irrigation or aspiration, can serve as a space for holding suture material S and/or needle N or as a portal for the introduction of other medical instruments such as, forceps, cutting members, ligators, or cautery devices. Also, channels 38a and 38c can be used for irrigation, aspiration, insertion of an instrument or the like by utilizing passages through inner member 44 of needle driver 40 and/or through inner member 44' of needle catcher 50. Proximal apertures 90–93, having valves, seals or the like, are provided for access to operating channels 38a–38d respectively.

Needle driver 40 and needle catcher 50 can be modified to suture anatomical tissue with straight or slightly curved suture needles by shaping the jaw members appropriately to receive and hold the needle. Also, the jaw members can be rotatable on the arms to accept needle N more smoothly. Further, needle N can be held between jaw members 50A and 50B while extending along the lengthwise direction of instrument 30 during insertion. In this case needle N can be seated in grooves formed along grasping surfaces of jaw members 50A and 50B or jaw members 50A' and 50B'.

From the above, it will be appreciated that the suturing and tying instrument according to the present invention permits suturing of anatomical tissue and tying of suture material during minimally invasive or open procedures without the need for multiple instruments inserted through multiple puncture sites and without the need for tying a knot externally and pushing the knot through the instrument. The needle driver and needle catcher each are movable and operable to grasp and release a suture needle N so that the suture needle can be driven through anatomical tissue and so that a knot can be tied in the suture material without additional instruments and without releasing the needle.

While the needle driver and the needle catcher have been described herein as being controlled in concert, separate independent operating mechanisms, such as knobs and handles, can be used to provide independent control of the needle driver and the needle catcher. The needle holders need only be movable relative to one another to pass the needle. Therefore, one of the needle holders can be fixed. Any appropriate proximal controls can be used to accomplish the disclosed movement. For example, any of the proximal controls disclosed in applicant's copending applications incorporated herein by reference can be used. The needle holders can be moved in seriatim or in concert.

The needle driver and the needle catcher, i.e. the needle holders, can be of the same design or of different designs as each is capable of grasping and releasing a needle. Also, the needle holders can be disposed in various portions of the barrel. For example, the instrument can have any of the configurations disclosed in the copending applications incorporated herein. Further, the function of the needle driver and the needle catcher can be interchanged and suturing and tying can be accomplished in the opposite direction depending on whether the surgeon is right-handed or left-handed or other practical considerations. The needle holders can be of any configuration which permits passing the needle back and forth.

One or more lengths of suture material can be attached to the suture needle at any desirable location along the body or tip of the needle including, but not limited to, the proximal end of the needle, intermediate or medial portions of the needle body, or locations adjacent the tip of the needle. It will also be appreciated that the instrument according to the present invention can be used with any type of standard suturing needle including, but not limited to, needles having sharp or blunt tissue penetrating tips, and needles having tissue penetrating tips at opposite axial ends of a needle body.

The holding mechanisms of the needle catcher and the needle driver shown and described herein are merely exemplary of the types of needle holding mechanisms that can be used according to the present invention. Accordingly, the needle holders can have any suitable configuration for cooperatively grasping needles to suture anatomical tissue including, but not limited to, configurations wherein jaw members or other elements pivot, slide or otherwise move relative to one another to capture and release a needle. The jaw members can, for example, be of straight, curved or angled configuration and can be provided with ribs, grooves, slots and/or holes along grasping surfaces to assure a positive grip. The jaw members can also carry cutting members, such as slots with sharp edges or protruding blades, and can have opposed arcuate or concave portions for clamping tubular objects, such as organs, without compressing the objects. Also, more than two needle holding devices can be provided in the suturing and tying instrument as needed.

The mechanisms for moving the needle catcher and needle driver relative to one another are merely exemplary of the types of mechanisms that can be used to perform these functions and other mechanisms can be used. The particular length and curvature of the suture needles shown and described herein as well as any angular displacements of the needle driver and catcher shown and described herein are merely exemplary, and it will be appreciated that other needle lengths and angular displacements can be used. For example, the needle holders can be flexible and can be drawn into the barrel proximally to be placed in an insertion position. Also, the needle holders can move rotationally, arcuately, or through any appropriate path to accomplish suturing and knot tying.

One of the needle holders can be used as forceps, to grasp the tissue, during suturing or can contain a clip applicator. Therefore, the invention can be used for pickup and cutting, pickup and clipping, pickup and suturing, or lysis of adhesion procedures. Alternatively, a forceps device can be inserted through the operating channel formed in the shaft of one of the needle holders or another operating channel. The jaw members can be used as unipolar or bipolar cautery electrodes by being electrically insulated from other portions of the instrument and being coupled to an electrical power source by connector 110. Also, a button can be provided to switch the electric power from one set of jaw members to the other. Further, tissue can be clamped between adjacent needle holders or tissue can be retracted by placing adjacent needle holders between tissue portions and moving the needle holders apart. The tying procedure can be varied to accomplish tying of any desirable knot.

The components of the instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument. The barrel can be of any shape. For example, the barrel can have a round, triangular, polygonal, or irregular cross-sectional shape.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A suturing instrument for causing a needle having suture material attached thereto to pass through anatomical tissue and for tying a knot in the suture material to secure the suture material and retain tension in the suture material, said instrument comprising:

an elongated barrel extending along a longitudinal axis and having a distal end and a proximal end;

a needle driver having a needle holding member extending from said distal end of said barrel;

a needle catcher having a needle holding member extending from said distal end of said barrel; and means for manipulating said needle driver and said needle catcher to pass the needle from said needle driver to said needle catcher to cause the needle to pass through the anatomical tissue and for manipulating the needle driver and the needle catcher to pass the needle from one of said needle driver and said needle catcher to the other of said needle driver and said needle catcher to tie a knot in the suture material, respective ones of the needle holding members move arcuately about the longitudinal axis when manipulated.

2. An instrument as recited in claim 1 wherein said needle driver comprises a driver shaft and said needle catcher comprises a catcher shaft, said means for manipulating comprising means for rotating said driver shaft and means for rotating said catcher shaft and means for operating said needle holding members.

3. An instrument as recited in claim 2, said needle driver comprising a driver connecting member disposed on a distal end of said driver shaft, said needle holding member of said needle driver extending from said driver connecting member, said needle catcher comprising a catcher connecting member disposed on a distal end of said catcher shaft, said needle holding member of said needle catcher extending from said catcher connecting member.

4. An instrument as recited in claim 3 wherein said driver connecting member is a driver arm that extends from a distal end of said driver shaft in a direction substantially perpendicular to an axis of rotation of said driver shaft and said catcher connecting member is a catcher arm that extends from a distal end of said catcher shaft in a direction substantially perpendicular to an axis of rotation of said catcher shaft.

5. An apparatus as recited in claim 4 wherein said driver arm comprises a pair of driver arm members and said catcher arm comprises a pair of catcher arm members.

6. An instrument as recited in claim 5 wherein said needle holding member of said needle driver comprises a pair of driver jaw members and said needle holding member of said needle catcher comprises a pair of catcher jaw members, said means for manipulating further comprising a driver operating mechanism for moving said driver jaw members toward and away from one another and a catcher operating mechanism for moving said catcher jaw members toward and away from one another.

7. An instrument as recited in claim 2, further comprising:
a driver operating channel defined in said driver shaft and extending from said proximal end to said distal end.

8. An instrument as recited in claim 2, further comprising a catcher operating channel defined in said catcher shaft and extending from said proximal end to said distal end.

9. An instrument as recited in claim 6, wherein the longitudinal axis of said driver jaw members is parallel to and offset from the longitudinal axis of said driver shaft and the longitudinal axis of said catcher jaws is parallel to and offset from the longitudinal axis of said catcher shaft.

10. An instrument as recited in claim 2, said means for manipulating further comprising means for coordinating movement of said means for rotating said driver shaft, said means for rotating said catcher shaft, and said means for operating said holding members.

11. An instrument as recited in claim 1, further comprising a channel formed in said barrel, a free end of said suture material extending through said channel.

12. An instrument as recited in claim 1, further comprising a grasping instrument for grasping a free end of said suture material.

13. An instrument as recited in claim 1, wherein said grasping instrument extends through a channel formed in said barrel.

14. An instrument as recited in claim 1 wherein said means for manipulating moves said needle driver and said needle catcher simultaneously.

15. An instrument as recited in claim 1 wherein said means for manipulating moves said needle driver and said needle catcher in seriatim.

16. A method of suturing anatomical tissue using a length of suture material attached to a needle and tying a knot in the suture material to secure the suture material and retain tension in the suture material, said method comprising the steps of:
introducing a distal end of an instrument extending along a longitudinal axis and having a barrel, a needle driver, and a needle catcher into an area proximate the anatomical tissue;
grasping the needle with the needle driver;
positioning the anatomical tissue proximate a tip of the suture needle;
manipulating the needle driver in an arcuate manner about the longitudinal axis to cause a tip of the needle to penetrate the anatomical tissue;
grasping the needle with the needle catcher;
releasing the needle from the needle driver;
manipulating the needle catcher in an arcuate manner about the longitudinal axis to pull the needle entirely through the anatomical issue; and
tying a knot in the suture material by transferring the needle from one of the needle catcher and the needle driver to the other of the needle catcher and the needle driver.

17. A method as recited in claim 16, wherein said tying step comprises transferring the needle from the needle catcher to the needle driver and transferring the needle from the needle driver back to the needle catcher.

18. A method as recited in claim 16, wherein said tying step comprises moving the needle away from the tissue, transferring the needle from the needle catcher to the needle driver, manipulating the instrument to define a loop in the suture material, and transferring the needle from the needle driver to the needle catcher to cause the needle to pass through the loop.

19. A method as recited in claim 18, said tying step further comprising placing tension on a free end of said suture material to tighten the knot.

20. A method as recited in claim 19, wherein said step of placing tension comprises grasping the free end of the suture material with a grasping instrument.

21. A method as recited in claim 16 wherein the needle driver and the needle catcher are coupled to move simultaneously in said manipulating steps.

22. A method of suturing anatomical tissue using a length of suture material attached to a needle and tying a knot in the suture material to secure the suture material and retain tension in the suture material, said method comprising the steps of:
introducing a distal end of an instrument having a barrel, a needle driver, and a needle catcher into an area proximate the anatomical tissue;
grasping the needle with the needle driver;
positioning the anatomical tissue proximate a tip of the suture needle;
manipulating the needle driver to cause a tip of the needle to penetrate the anatomical tissue;
grasping the needle with the needle catcher;
releasing the needle from the needle driver;
manipulating the needle catcher to pull the needle entirely through the anatomical tissue; and
tying a knot in the suture material by transferring the needle from one of the needle catcher and the needle driver to the other of the needle catcher and the needle driver, wherein the needle driver comprises a driver shaft extending through at least a portion of the barrel, a driver connecting member extending from a distal end of said driver shaft, and driver jaw members disposed on the driver connecting member and having a longitudinal axis that is offset from a longitudinal axis of the driver shaft, and the needle catcher comprises a catcher shaft extending through at least a portion of the barrel, a catcher connecting member extending from a distal end of the catcher shaft, and catcher jaw members disposed on the catcher connecting member and having a longitudinal axis that is offset from a longitudinal axis of the catcher shaft, said manipulating steps and said tying step comprising rotating at least one of the catcher shaft and the driver shaft.

23. A method of suturing anatomical tissue using a length of suture material attached to a needle and tying a knot in the suture material to secure the suture material and retain tension in the suture material, said method comprising the steps of:
introducing a distal end of an instrument having a barrel, a needle driver, and a needle catcher into an area proximate the anatomical tissue;
grasping the needle with the needle driver;
positioning the anatomical tissue proximate a tip of the suture needle;
manipulating the needle driver to cause a tip of the needle to penetrate the anatomical tissue;

grasping the needle with the needle catcher;

releasing the needle from the needle driver;

manipulating the needle catcher to pull the needle entirely through the anatomical tissue; and tying a knot in the suture material by transferring the needle from one of the needle catcher and the needle driver to the other of the needle catcher and the needle driver, wherein the needle driver and the needle catcher move independently in said manipulating steps.

24. A method of suturing anatomical tissue using a length of suture material attached to a needle and tying a knot in the suture material to secure the suture material and retain tension in the suture material, said method comprising the steps of:

introducing a distal end of an instrument having a barrel, a needle driver, and a needle catcher into an area proximate the anatomical tissue;

grasping the needle with the needle driver;

positioning the anatomical tissue proximate a tip of the suture needle;

manipulating the needle driver to cause a tip of the needle to penetrate the anatomical tissue;

grasping the needle with the needle catcher;

releasing the needle from the needle driver;

manipulating the needle catcher to pull the needle entirely through the anatomical tissue; and tying a knot in the suture material by transferring the needle from one of the needle catcher and the needle driver to the other of the needle catcher and the needle driver by moving the needle away from the tissue, transferring the needle from the needle catcher to the needle driver, manipulating the instrument to define a loop in the suture material, transferring the needle from the needle driver to the needle catcher to cause the needle to pass through the loop, and placing tension on a free end of said suture material to tighten the knot, wherein the free end of the suture material extends through a channel formed in the barrel to a proximal end of the instrument and said step of placing tension comprises grasping the free end of the suture material from the proximal end.

25. A method of suturing anatomical tissue using a length of suture material attached to a needle and tying a knot in the suture material to secure the suture material and retain tension in the suture material, said method comprising the steps of:

introducing a distal end of an instrument having a barrel, a needle driver, and a needle catcher into an area proximate the anatomical tissue;

grasping the needle with the needle driver;

positioning the anatomical tissue proximate a tip of the suture needle;

manipulating the needle driver to cause a tip of the needle to penetrate the anatomical tissue;

grasping the needle with the needle catcher;

releasing the needle from the needle driver;

manipulating the needle catcher to pull the needle entirely through the anatomical tissue; and tying a knot in the suture material by transferring the needle from one of the needle catcher and the needle driver to the other of the needle catcher and the needle driver by moving the needle away from the tissue, transferring the needle from the needle catcher to the needle driver, manipulating the instrument to define a loop in the suture material, transferring the needle from the needle driver to the needle catcher to cause the needle to pass through the loop, and placing tension on a free end of said suture material to tighten the knot by grasping the free end of the suture material with a grasping instrument which extends through a channel defined in the barrel.

* * * * *